(12) United States Patent
Fernandez et al.

(10) Patent No.: US 8,801,615 B2
(45) Date of Patent: Aug. 12, 2014

(54) SYSTEM AND METHOD FOR ULTRASOUND THERAPY TREATMENT

(75) Inventors: Anna Theresa Fernandez, Falls Church, VA (US); Balasundara Raju, Tarrytown, NY (US)

(73) Assignee: Koninklijke Philips N.V., Eindhoven (NL)

( * ) Notice: Subject to any disclaimer, the term of this patent is extended or adjusted under 35 U.S.C. 154(b) by 160 days.

(21) Appl. No.: 13/119,810

(22) PCT Filed: Sep. 14, 2009

(86) PCT No.: PCT/IB2009/054010
§ 371 (c)(1),
(2), (4) Date: Mar. 18, 2011

(87) PCT Pub. No.: WO2010/038162
PCT Pub. Date: Apr. 8, 2010

(65) Prior Publication Data
US 2011/0178391 A1    Jul. 21, 2011

Related U.S. Application Data

(60) Provisional application No. 61/101,230, filed on Sep. 30, 2008.

(51) Int. Cl.
*A61N 7/00* (2006.01)
(52) U.S. Cl.
USPC ........... 600/439; 600/407; 600/411; 600/412; 600/427; 600/436; 600/466; 601/2; 601/3
(58) Field of Classification Search
USPC .......... 601/2–4; 600/407, 411, 412, 427, 439, 600/436, 462, 466
See application file for complete search history.

(56) References Cited

U.S. PATENT DOCUMENTS

| | | | |
|---|---|---|---|
| 2006/0079816 A1 * | 4/2006 | Barthe et al. | 601/2 |
| 2008/0264716 A1 | 10/2008 | Kuiper | |

FOREIGN PATENT DOCUMENTS

| | | |
|---|---|---|
| WO | WO0182778 | 11/2001 |
| WO | WO03069380 | 8/2003 |
| WO | WO2005122139 | 12/2005 |
| WO | 2006042163 A3 | 4/2006 |
| WO | WO 2007125500 A2 * | 11/2007 |
| WO | WO 2008084455 A1 * | 7/2008 |
| WO | WO 2008090504 A1 * | 7/2008 |
| WO | 2008098101 A2 | 8/2008 |

* cited by examiner

OTHER PUBLICATIONS

M. Burtnyk et al., "TI Simulation of MRI-Guided Transurethral Conformal 3-D Ultrasound Therapy of the Prostate", 6th International Symposium on Therapeutic Ultrasound, Aug. 30-Sep. 2, 2006, Oxford, England.

*Primary Examiner* — Ruth S Smith (57) ABSTRACT

A system and method for treating tissue uses an ultrasound therapy system including an ultrasonic applicator having has at least one transducer element. Steering and focusing of ultrasound beams uses at least one variable focus lens, which may be a fluid focus lens, attached to each transducer element so that focus of the variable focus lens is controlled by a voltage signal. A treatment controller receives input from an imager and controls the voltage applied to the variable focus lens. The treatment controller controls the lens voltage signals, at least partially determined by the input from the imager, and directs an ultrasonic treatment beam emitted by the transducer element. Fine adjustment of the therapy beam is achieved to deliver therapy for various prostate sizes and shapes while avoiding damage to critical structures such as the rectal wall and nerve bundles.

18 Claims, 7 Drawing Sheets

SYSTEM AND METHOD FOR ULTRASOUND THERAPY TREATMENT

The present application relates to the therapeutic arts, in particular to systems and methods for ultrasound therapy treatment, most particularly for prostate treatment.

Prostate cancer is among the leading causes of morbidity and mortality in the world. According to the American Cancer Society (ACS), there will be an estimated 220,000 new cases of prostate cancer in 2007, making it the second most frequently diagnosed cancer in American men after non-melanoma skin cancer. It is also estimated that 27,000 men will die of this disease in 2007 in the US. Prostate cancer is not purely a western world disease and is among the top 5 cancers diagnosed worldwide. Benign prostatic hyperplasia (BPH), or enlarged prostate, is another prostate disease and is characterized by genitourinary symptoms. Studies have shown that 50% of all males in their fifties and 90% of males in their nineties exhibit some pathological evidence of BPH.

The high incidences of both prostate cancer and BPH have prompted increased investigation into the treatment of these diseases. Currently accepted treatments for prostate cancer include radical prostatectomy, external beam radiation therapy, brachytherapy, cryotherapy, hormone therapy and chemotherapy. All of these therapies have their associated side effects either due to the invasive nature, non-specific treatment, use of ionizing radiation, or the inability to identify and target the localized cancer during the procedure. In addition, the side effects (incontinence, impotence, bowel problems) associated with current therapies limit their use. Many weaknesses of current prostate cancer therapies are addressed by therapeutic ultrasound e.g. high intensity focused ultrasound (HIFU), especially with image guidance. HIFU for the prostate is minimally-invasive, provides non-ionizing ablative therapy to any location within the prostate, and, when coupled with image-guidance, allows real-time therapy guidance to specifically identified localized cancer sites in and around the prostate. Moreover, it can be used as an adjuvant therapy to radiation and to localize delivery of emerging drugs to the prostate.

Current approaches to ultrasound ablation of the prostate include transrectal devices that have been approved in Europe and several countries around the world (Rewcastle 2006). The limitation of these devices include long treatment time (longer than 3 to 4 hours), inability to treat large prostates (ones having anterior-posterior distance larger than 2.5 cm or 4 cm depending on the manufacturer), and impotence rates as high as 60% (although still lower than alternative techniques that report 90%). The overall prostate volume treated with these devices needs to be less than 40 cc, and in many cases, prior reduction of the size is done through the use of hormonal therapies or TURP (trans-urethral resection of the prostate). Other limitations are that the therapeutic ultrasound is distorted by the rectal wall before reaching the prostate and the possibility of near-field heating of the rectal wall.

To overcome the above-mentioned difficulties, transurethral ultrasound applicators have been proposed in which single element transducers are inserted into the urethra to insonify the region in front of it, and sometimes rotated to cover the full cross-section. A transurethral design is advantageous since it provides direct acoustic access to the prostate gland without the effects of intervening tissues. In practice, several transducers are placed along the urethral axis in order to cover the 3D volume.

Currently due to space limitations in the urethra, transurethral transducers use only one or a few single element transducers. This makes it impossible to adjust the steering or focusing of the beam in order to target specific regions in the prostate, as is usually done with electronic focusing multiple elements (typically up to 128 elements in a conventional ultrasound imaging array). Lack of beam steering makes it difficult to avoid damaging sensitive structures such as the nerve bundles while targeting tumor regions in the prostate. While mechanical rotation can be used to move the beam to different regions in the prostate along the cross-section, and translation can be used to move the beam along the axis of the prostate, mechanical motion cannot move the beam along the ultrasound propagation dimension (axial direction) from the urethra to the prostate capsule.

Thus, the single-element therapy transducers currently manufactured have either a flat surface or a curved surface/mechanical lens (concave or convex) in order to induce a fixed focus on the lens. This transducer focus cannot be changed once manufactured.

Fluid Focus technology is a solution described in WO 03/069380 and WO 2005/122139 for the purpose of allowing light to be focused through alterations in the physical boundaries (i.e. the meniscus) of a fluid filled cavity with specific refractive indices. A process known as electrowetting, wherein the fluid within the cavity is moved by the application of a voltage across conductive electrodes, accomplishes the movement of the surface of the fluid. This change in surface topology allows light to be refracted in such a way to alter the travel path to cause focusing.

Ultrasound propagates in a liquid medium; in fact, the human body is often referred to as a liquid incapable of supporting high frequency ultrasonic waves other than compressional waves. In this sense, the waves are sensitive to distortion by differences in ultrasonic speed of propagation in bulk tissue, but also by abrupt changes in speed of sound at interfaces. This property is one that is exploited in this invention, which calls for the ability to use an adjustable liquid lens (such as a Fluid Focus lens) with two liquids possessing differing acoustic speed such that by changing the shape of the interface between the liquids, one can control the position of the focus and the direction of ultrasound wave propagation.

The Summary is provided to comply with 37 C.F.R. §1.73, requiring a summary of the invention briefly indicating the nature and substance of the invention. It is submitted with the understanding that it will not be used to interpret or limit the scope or meaning of the claims.

In accordance with one aspect of the exemplary embodiments, a system for delivering ultrasound therapy to a tissue is described. The system includes an ultrasonic applicator including at least one transducer element. At least one variable focus lens is attached to the transducer element, wherein focus of the variable focus lens is controlled by a voltage signal. An imaging means is included for acquiring images of the tissue to be treated. A motion controller that can move the ultrasonic applicator in at least one of a rotational direction and an axial direction is also provided, together with a treatment controller that receives input from the imaging means and controls the voltage applied to the variable focus lens. The treatment controller controls the lens voltage signals, at least partially determined by the input from the imaging means, and serves to direct an ultrasonic treatment beam emitted by said at least one transducer element.

In this invention, fluid focus lenses are preferably used, which enable adjustments in the transducer focus during scanning procedures to control axial, lateral, or elevation focus on single or few-element transducers. The ultrasonic applicator can be configured for transurethral accessed treatment (for example, of the prostate), and the variable focus lens allows the therapy transducer to direct therapy beams deeper in the prostate and deliver therapy along more directions (span therapy angle beams laterally and in elevation) before having to rotate the transducer to a new area—thus increasing accuracy of therapy delivery and reducing therapy time.

The invention also enables fine adjustment of the therapy beam to deliver therapy for various prostate sizes and shapes while avoiding damage to critical structures such as the rectal wall and nerve bundles. The same element can be used to create both diverging beams for a slow and conservative treatment (e.g. towards posterior side) as well as converging beams for faster and/or deeper treatment (e.g. towards anterior side).

In one arrangement, the fluid focus lens can comprise a plurality of fluid focus lens elements arranged on a transducer element. In a preferred arrangement, a plurality of transducer elements can be provided in the ultrasonic applicator. The plurality of transducer elements are preferably arranged axially along an elongate ultrasonic applicator. In some arrangements, a single variable focus lens can be used to cover a plurality of transducer elements, such as neighboring elements. Some arrangements may include a combination of transducer elements and variable focus lenses in a single applicator, for example some of the transducer elements may have a variable focus lens made of a plurality of fluid focus lens elements, some may have a single variable focus lens, and some may include one variable focus lens covering two or more transducer elements. The precise arrangement of lenses and elements can be selected and altered to suit the desired application.

The imaging means can provide at least one of pre-treatment planning images and feedback images during treatment. The imaging means can be any suitable imaging means. For example, the imaging means can be one or more of the following: an intermittent ultrasonic imaging beam emitted by said at least one transducer element, an endo-rectal or vaginal ultrasound imaging system, an ultrasound imaging system having an external transducer, a magnetic resonance imaging system with or without the capability to perform MRI thermometry, a PET imaging system, a CT imaging system, a contrast-enhanced imaging system, a thermal monitoring system, and/or a tissue elasticity monitoring system, and any combinations thereof.

The treatment controller may further control a driving signal to the at least one transducer element at least partially determined by the input from the imaging means. A user interface can be provided to enable an operator to visualize images from the imaging means and to modify the actions of the treatment controller.

In accordance with another aspect of the exemplary embodiments, a method of treating a tissue is described, which involves placing an ultrasonic applicator with one or more ultrasound transducer elements near to the tissue of interest. The method further involves exciting at least one of the ultrasound transducer elements with a driving signal, and monitoring the effect of treatment through an imaging means. The focus of at least one of the ultrasound transducer elements can be controlled by adjusting the voltage applied to a variable focus lens attached to the ultrasound transducer element based on information from the imaging means. The method further includes moving or rotating the ultrasonic applicator to cover therapy at substantially different regions in the tissue.

In a preferred arrangement, the variable focus lens is a fluid focus lens. The ability to adjust the focus of the beam has various advantages. For example, the capability to steer the beam makes it possible to move the beam out of the treatment plane and avoid dead-spots in between the element positions without the need for mechanical translation.

The method can further include obtaining planning images of the tissue to be treated prior to treatment, in addition to the monitoring images during treatment. The imaging means can provide at least one of ultrasound images, magnetic resonance images, magnetic resonance thermometry images, PET images, CT images, thermal monitoring images, and tissue elasticity monitoring images, and any combinations thereof.

A user interface can be provided to enable an operator to visualize images from the imaging means and to modify the actions of a treatment controller that controls the voltage applied to the variable focus lens. The movement and/or rotation of the ultrasonic applicator can be controlled by a treatment controller, modifiable by the operator.

The method can also involve controlling the driving signal to the at least one ultrasound transducer element at least partially based on information from the imaging means, controlling at least one of a respective amplitude, frequency and phase of the signal. Thus, both the focus of the beam and the strength and frequency of the beam can be controlled at the same time.

The above-described and other features and advantages of the present disclosure will be appreciated and understood by those skilled in the art from the following detailed description, drawings, and appended claims.

The exemplary embodiments of the present disclosure are described with respect to ultrasound therapy of a human. It should be understood by one of ordinary skill in the art that the exemplary embodiments of the present disclosure can be applied to other types of ultrasound therapy and other portions of the body, whether human or animal. The use of the method and system of the exemplary embodiments of the present disclosure can be adapted for application to other types of applicators.

Figure 1:
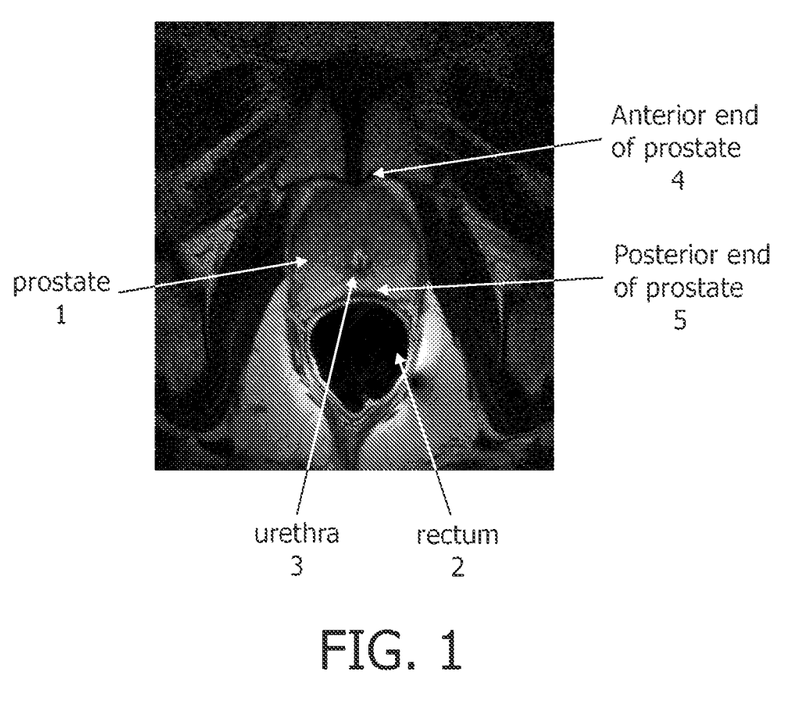
FIG. 1 is a MR image of a prostate in the transverse cross-section.

Referring to the drawings, FIG. 1 shows a cross-section of a prostate (1) and rectum (2) wherein it is seen that the distance from the urethra (3) to the edge of the prostate (capsule) is not uniform. In general the distance from the urethra (3) to the anterior end (4) is larger (e.g., 3 cm) than the distance to the posterior end (5) where most cancers originate. When the urethra-to-prostate capsule distance is short, a physician might prefer to use a divergent beam that can provide slower and more conservative treatment. On the other hand when the urethra-to-prostate capsule distance is large, a physician may prefer to use focused beams that can provide increased penetration of the therapy beam and/or reach the desired locations further away from the transducer.

Figure 2:
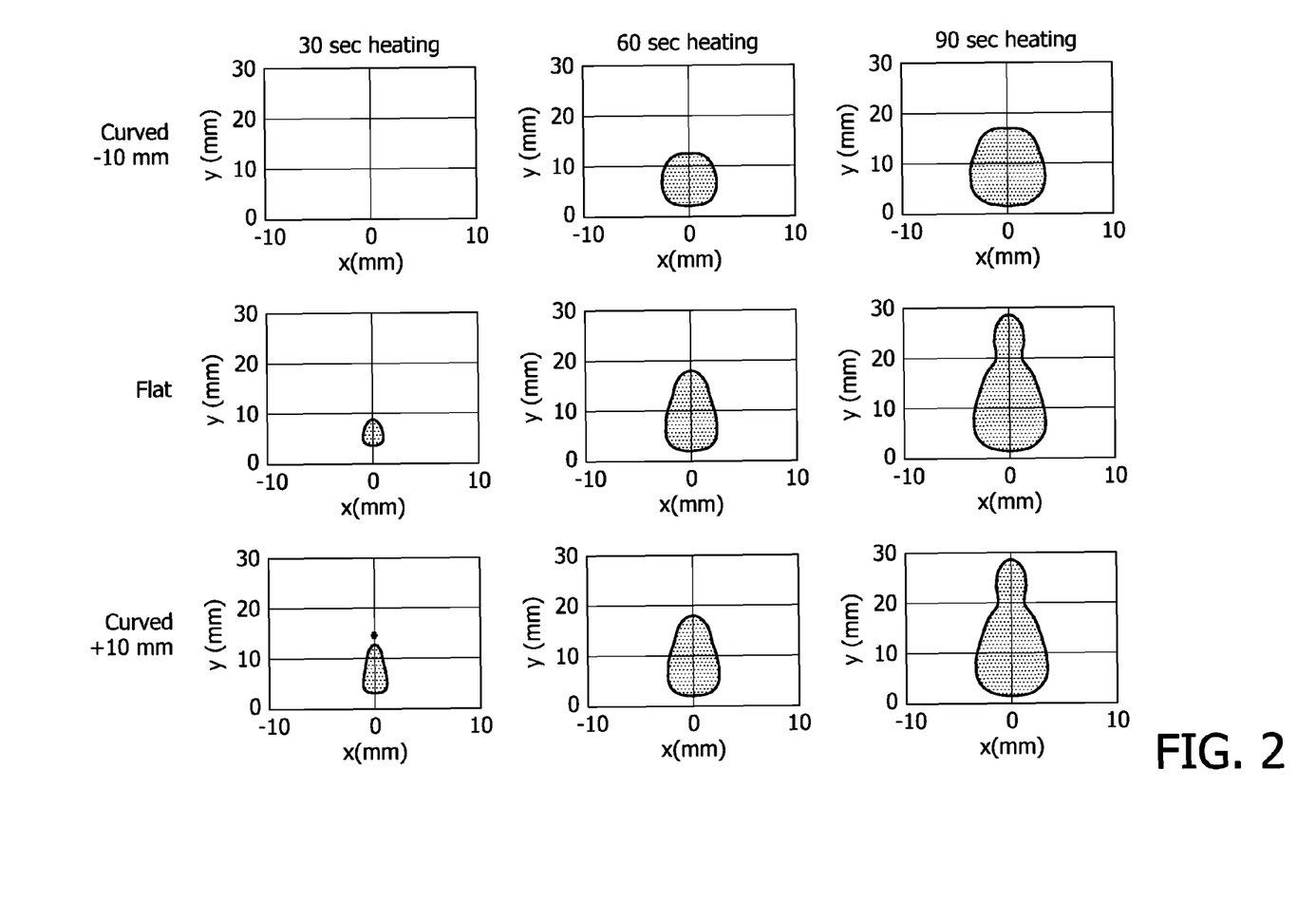
FIG. 2 shows an effect of element curvature on thermal dose patterns for the case of three different curvatures. The y-axis is the direction of propagation of the ultrasound beam.

FIG. 2 shows simulations of thermal dose contours (240 minutes at 43° C.) for different element curvatures on elements (transmitting at 4 MHz CW) to illustrate the above concept. The top row shows the case of heating from a 4×10 mm (lateral×elevation) element with a curvature of −10 mm, leading to diverging beams. The curvature is along the x (lateral) direction and the element is flat along the z direction (into the paper, i.e. elevation direction). The middle row shows the thermal dose from an element of the same size but having no curvature (i.e. flat). The bottom row shows the thermal dose from an element of the same size but having a curvature of +10 mm leading to converging beams. The different columns show the effect of different sonication durations: 30, 60, or 90 seconds, all with a subsequent cooling phase of another 30 seconds. It can be seen that the diverging beam is advantageous when a conservative and slow treatment is preferred (e.g. to carefully monitor thermal dose near rectal wall or nerve bundles). On the other hand, a converging beam may be advantageous when treating deeper distances and when there is no concern of damaging critical structures (e.g. towards the anterior side of the prostate) since it leads to faster treatments.

The exemplary embodiments of the invention utilize an ultrasonic transducer, either single or multiple elements, with single or multiple fluid focus ultrasonic lenses placed above the element(s). The lens may consist of two liquids with matching impedances, but differing speed of sounds. This allows for maximum forward propagation while allowing for control over the direction of the ultrasonic beam. The liquid in the lens cavity will have a speed of sound chosen to maximize flexibility in the focusing and refraction of the ultrasonic signal. The fluid lens can incorporate two or more electrodes positioned to allow control of the surface topology of the meniscus that in turn will allow control of the refraction of the ultrasonic beam.

Figure 3A:
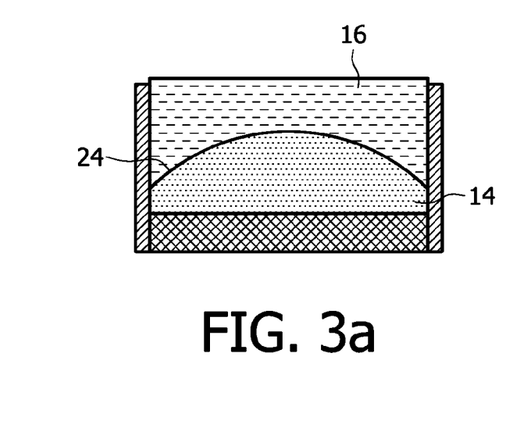
FIG. 3a-3d show a subset of lens formations made with fluid focus lens technology.
Figure 3B:
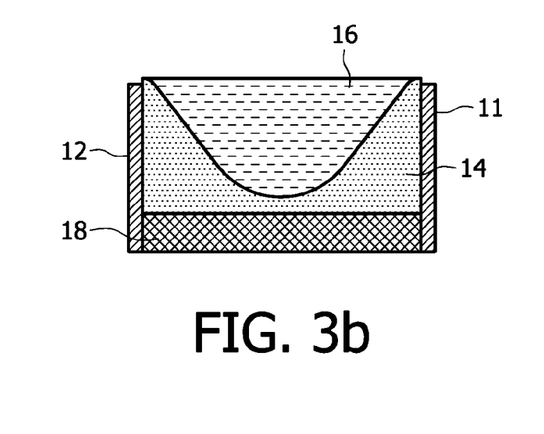
Figure 3C:
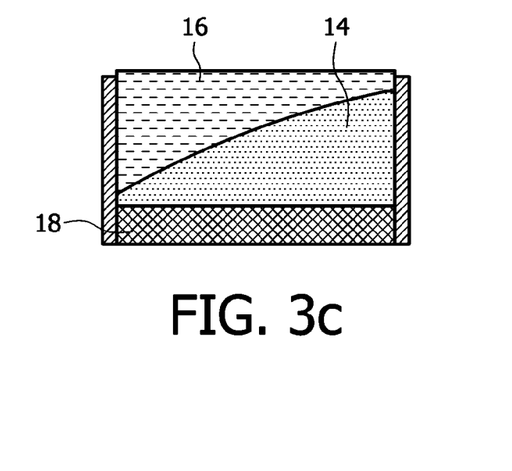
Figure 3D:
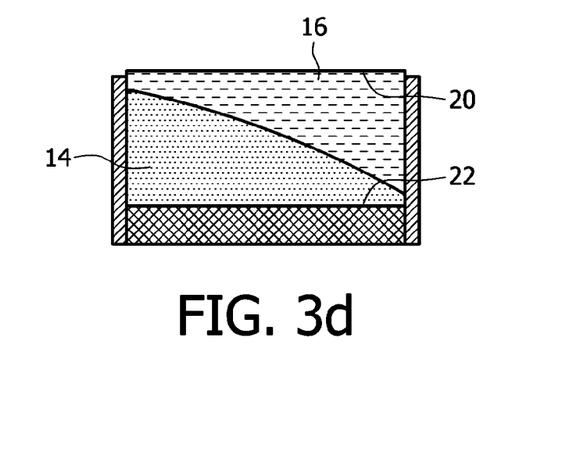

FIGS. 3a-3d show a subset of lens formation using a fluid focus lens 10. The voltage across the electrodes 11, 12 changes the surface between the 2 liquids (in this case, oil 14 and water 16) to form different lens configurations that will change focus along the axial direction (direction of propagation) or steer the therapy beam emitted from transducer 18. The liquids are placed between two thin coupling film layers 20, 22 to avoid escape of the fluids. A converging lens (shown in FIG. 3a) is created when the meniscus 24 between the oil 14 and water 16 (or other liquids used in the lens) is forced to form a convex shape due to the action of the electrodes 11, 12 on the electrically conductive water 16. Similarly a diverging lens is created (shown in FIG. 3b) when the oil is forced to form a concave shape. As shown in FIGS. 3c and 3d, steering lenses can be formed when the meniscus 24 is forced into an approximately triangular configuration.

The curvature of the meniscus 24 can be induced along one dimension or across the two dimensions of the element depending on the number of electrode pairs used to induce the voltage change—thus flat, hemispherical, or cylindrical-shaped lenses can be generated. The lens changes can occur in real-time during a treatment procedure (through voltage changes controlled by an external control system)—enabling focus control along the direction of propagation of the therapy beam as well as steering of the therapy beam. The therapy beam can then be steered not only along the lateral dimension but also in elevation.

Figure 4A:
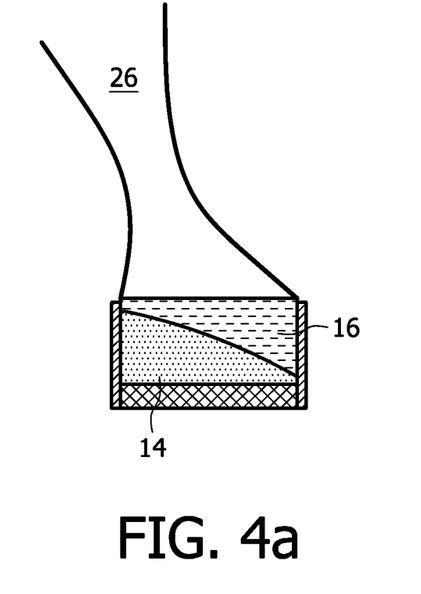
FIG. 4a-4d shows example scenarios of steering capabilities with fluid focus lens technology.
Figure 4B:
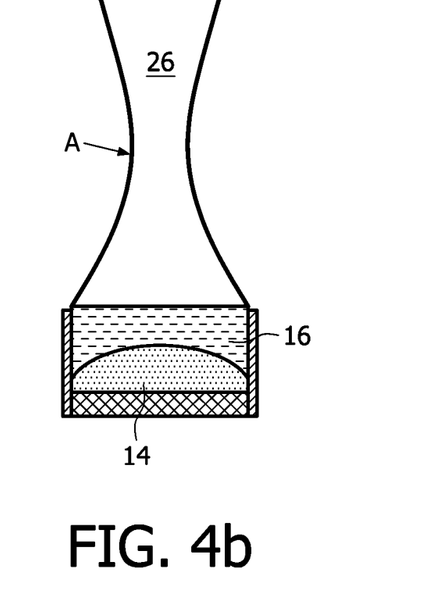
Figure 4C:
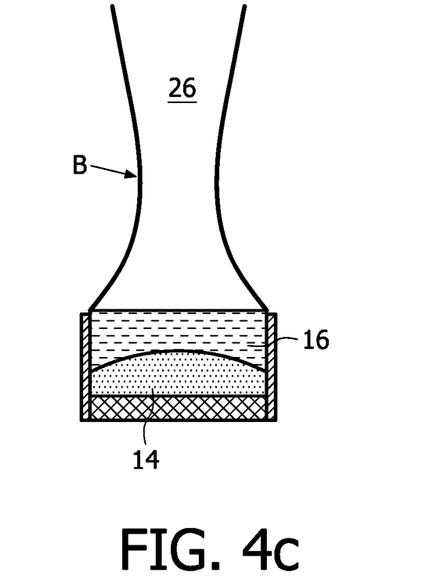
Figure 4D:
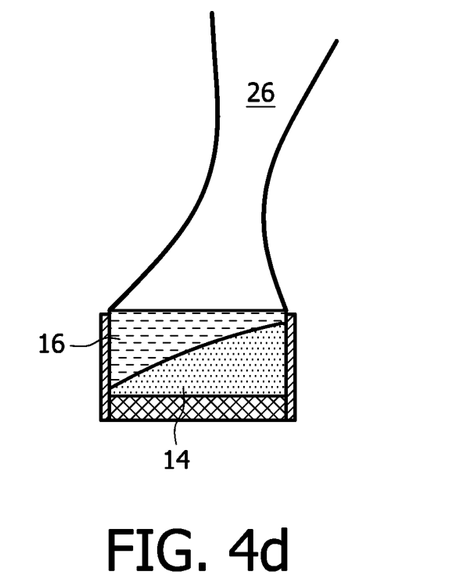

FIGS. 4a-4d show example steering configurations capable with fluid focus lens technology, used with an ultrasound therapy beam 26. A steering lens as shown in FIG. 4a can steer the beam left, or up/down along the elevation dimension. A steering lens as shown in FIG. 4d can steer the beam to the right. Using a converging lens as shown in FIG. 4b, the beam 32 can be axially focused at point A, whereas by altering the convex shape of the meniscus 24, the point of focus of the beam 26 can be altered to point B, as shown in FIG. 4c. The fluid lens changes can be made in real time while the ultrasound therapy beam 26 is being emitted, thus changing the focus of the beam as needed to reach areas of the prostate that the physician desires to treat.

Figure 5A:
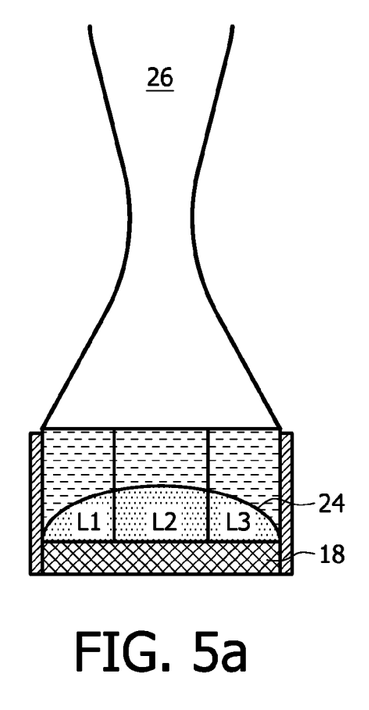
FIGS. 5a and 5b show examples of the use of 3 lenses (L1, L2, and L3) to control the beam aperture.
Figure 5B:
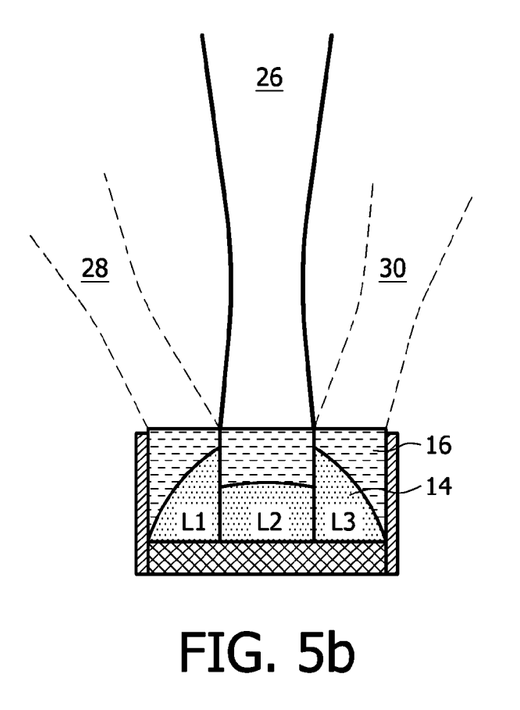

FIGS. 5a and 5b illustrate the use of three fluid focus lenses L1, L2 and L3 to control the aperture of the beam 26. The lenses L1, L2 and L3 are placed side-by-side over a single transducer 18. By separately controlling the three sets of electrodes, 11, 12, a system can be created whereby either the full aperture is used as shown in FIG. 5a, or by making lens L1 into a left-steering lens, and lens L3 into a right-steering lens, as shown in FIG. 5b, most of the beam energy can be focused through lens L2 to use a smaller aperture for the on-axis beam 26. Lower energy beams 28, 30 are created from lenses L1, L3 which diverge from the on-axis beam and have less energy than the main beam 26, which do not interfere with treatment due to the low energy.

Figure 6:
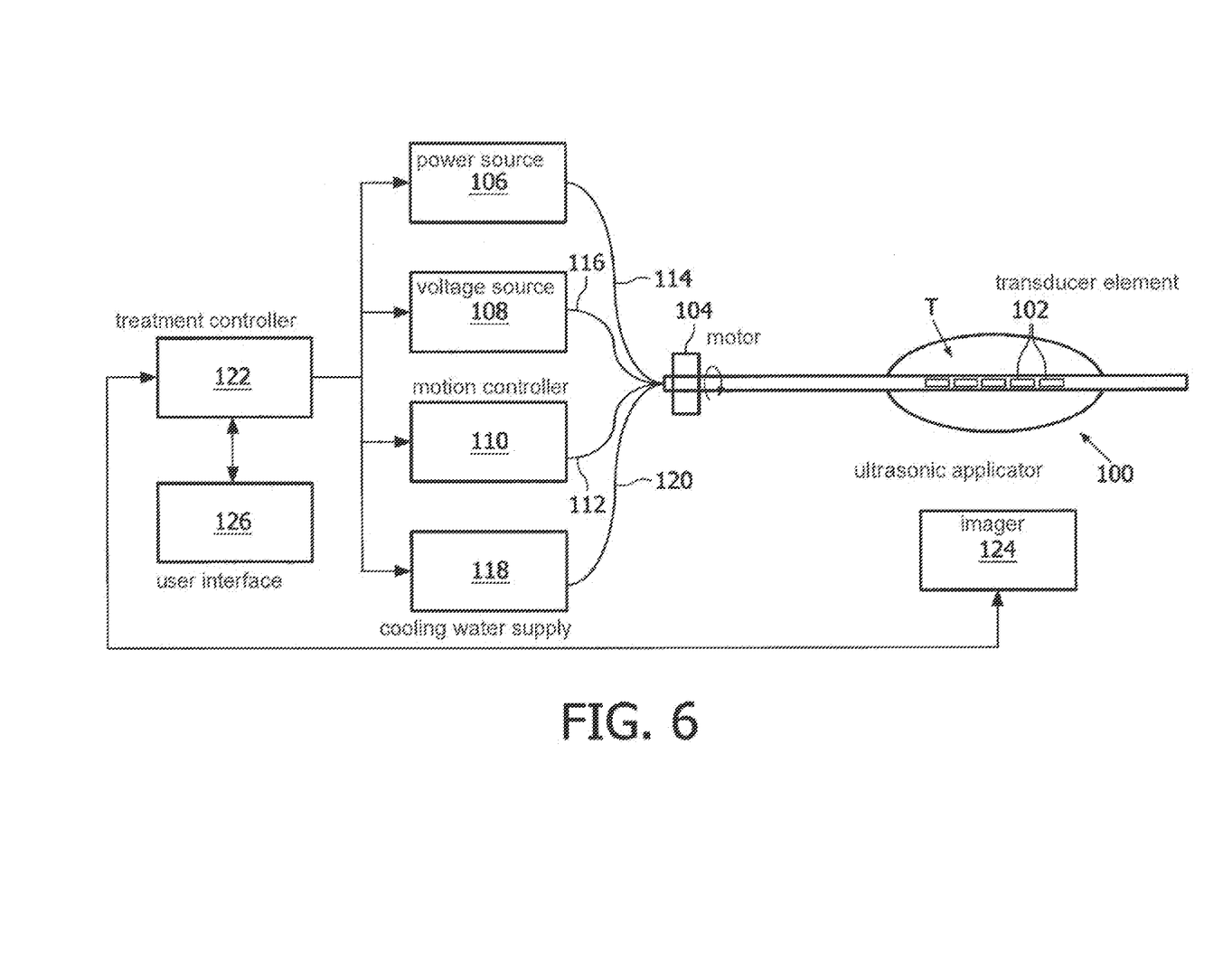
FIG. 6 is a schematic representation of an ultrasound therapy system with elements controlled by fluid focus lenses according to the present invention.

A system for treating prostate diseases using a transurethral ultrasound therapy and/or imaging system is shown in FIG. 6. The steering and focusing of ultrasound beams is done with the aid of fluid focus lens technology, as previously described. The invention enables fine adjustment of an ultrasound therapy beam to deliver therapy for various prostate sizes and shapes while avoiding damage to critical structures such as the rectal wall and nerve bundles. The same element can be used to create both diverging beams for a slow and conservative treatment (for example, towards posterior side) as well as converging beams for faster and/or deeper treatment (for example, towards anterior side).

Referring to FIG. 6, the system may include an ultrasonic applicator 100 with a plurality of ultrasound transducer elements 102, and which may be movable using a motor 104. For example, eight ultrasound transducer elements 102 may be provided in an applicator, although it will be appreciated that the number of elements is variable. Each transducer element 102 can supplied with a fluid focus lens 10 (not shown separately in FIG. 6), or, for example, a single fluid focus lens 10 can be provided to cover two or more adjacent transducer elements 102 or, in other arrangements, multiple fluid focus lenses 10 can be used with a single transducer element 102. The applicator 100 is placeable in or adjacent to the tissue to be treated, T, such as the prostate. Various control elements may be connected to the applicator 100, including a power source 106 for exciting the transducer elements 102, and a voltage source 108 for controlling a fluid focus lens attached to each element 102. The system can also include a motor drive and motion controller 110 that can move and/or rotate the applicator by controlling the motor 104. The components 104, 106 and 108 can be connected to the applicator 110 by cables 112, 114 and 116 respectively. A cooling water supply 118 may optionally also be included so that water can be circulated close to the transducer elements 102 via hose 120.

A treatment controller 122 can be provided, that controls the actions of the components 104, 106, 108 and 110 and that receives input from an imaging subsystem 124 for acquiring planning images and/or feedback images for monitoring the treatment (for example, through ultrasound or MR imaging or any other suitable imaging system, or thermal monitoring or other image information monitoring methods that assess the mechanical changes in the tissue in response to the treatment). The treatment controller 122 controls the excitation signal to the transducer elements and the voltage applied to the fluid focus lens to deliver therapy to the prostate. The treatment controller 122 may control the movement of the applicator in order to position the therapy beam at the intended target location. The treatment controller 122 may be connected to a user interface 126 so that it may be operated by a physician operator.

In a first embodiment, one or more fluid focus based elements 102 can be arranged along the circumference of the urethra constituting one row of elements to be used for therapy. Several rows of elements can arranged along the axis of the applicator 100, for example, eight rows of elements 102 can be used. The urethra typically has a diameter of approximately 6 mm, and so the number of elements in a row can depend upon the size of the elements. Additionally, it should be noted that the height of the fluid focus lens 10 relative to its width affects the degree of focusing that can be achieved, and so the size considerations should be carefully considered to ensure an adequate tradeoff between the number and size of transducer elements 102 with attached fluid focus lenses 10 desired, and the degree of focusing desired. A transducer transmit frequency of operation is preferentially approximately 4 MHz (CW or substantially high duty cycle), although any frequency from approximately 0.5 to approximately 20 MHz may be used. The therapeutic elements can be embedded in a balloon that can be filled with water or fluid for acoustic coupling. The choice of the two or more fluids (density, sound speed, lens-to-transducer, lens-to-external fluid layers) in the lens system can be chosen such that there will be no disruption of the lens by the energy of the therapy beam.

In addition, the fluid focus lens 10 can be placed on top of a mechanically curved transducer element. In this case, the fluid focus lens 10 will enable localized adjustments of the focus about the fixed transducer element focus and allow for elevation or lateral therapy beam steering.

Figure 7:
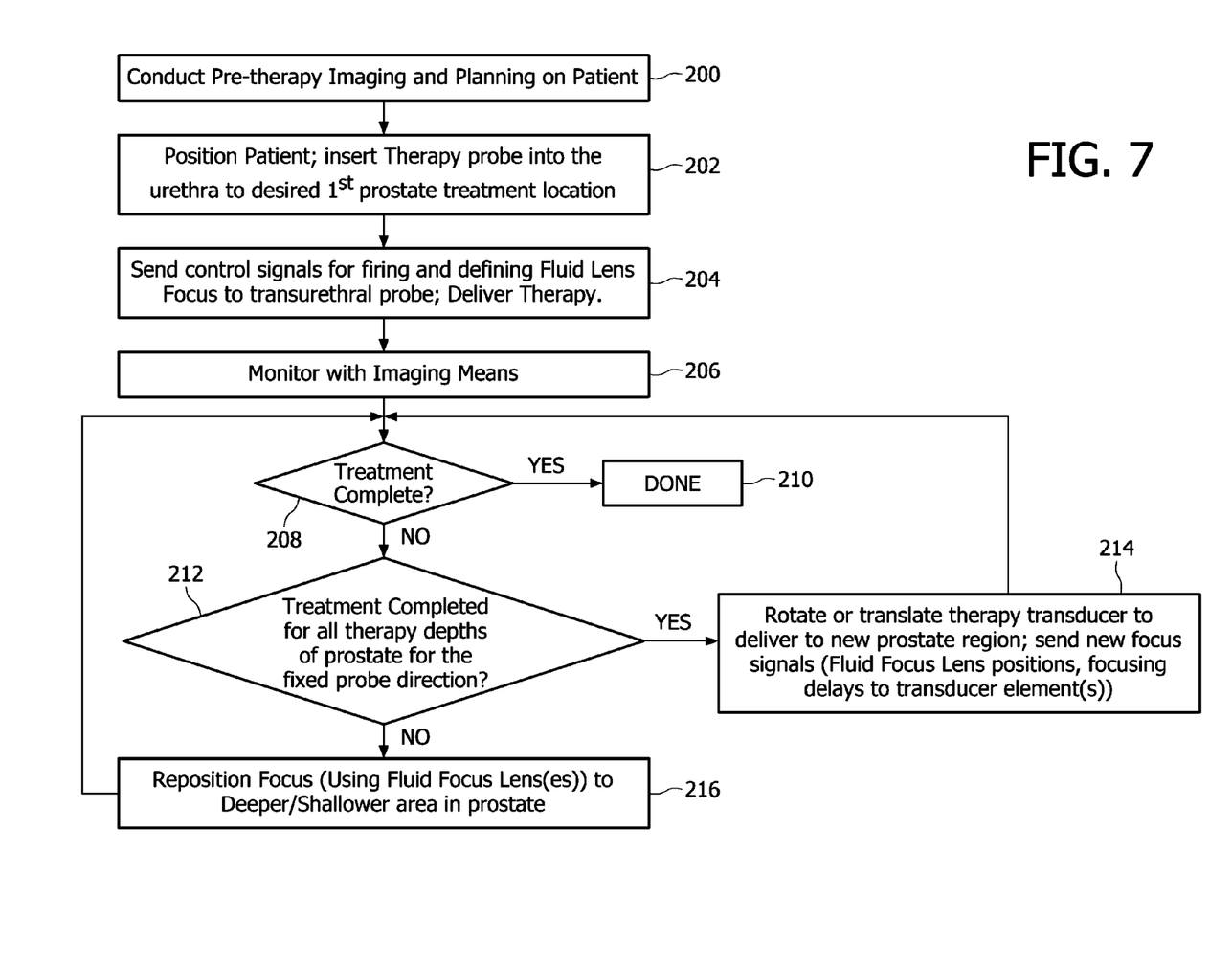
FIG. 7 is a flow chart describing an embodiment of therapy delivery/feedback in clinical environment.

An exemplary method for prostate therapy delivery is described with reference to FIG. 7. At a first step 200, pre-therapy imaging and planning is conducted. This may involve conventional ultrasound images (e.g. B scans) which can be obtained and provided to the operator who chooses the treatment volumes (whole prostate or a portion of it). Such imaging may be conducted using endo-rectal transducers, external transducers, etc. Alternatively, magnetic resonance imaging system, PET, CT, contrast imaging and various other techniques involving ultrasound and MR can be employed. Ultrasound imaging can be done through endorectal transducers or external transducers. The pre-therapy imaging and planning can be conducted days before the therapy, at the discretion of the treating physician.

At step 202, once the patient is appropriately positioned and sedated as desired, the therapy probe is inserted into the urethra to a desired first prostate treatment location. The operator then sets the fluid focus lens to a deep focal location by using the treatment controller 122 via the user interface 126 to send the control signals for defining the appropriate fluid focus lens to begin prostate therapy of the anterior portion of the prostate at step 204. Therapy is then administered at this location, while monitoring with an imaging means at step 206 to ensure the correct progression of treatment. The imaging means provides feedback during treatment and may be a separate ultrasound transducer, magnetic resonance imaging system, PET, CT, contrast imaging and various other techniques involving ultrasound and MR, including US or MR thermometry. Such imaging may be conducted using endo-rectal transducers, external transducers, etc., as for the pre-planning imaging. In some embodiments, temperature feedback can be used instead of or in addition to ultrasound or other imaging to give feedback to the operator (e.g. anatomical, functional, or mechanical stiffness information). Alternatively, the therapy transducer itself can be configured to intermittently image the prostate during treatment.

At step 208, the treatment is reviewed to see if it is complete. If it is complete, the treatment can stop at this point (step 210). If it is not complete, step 212 questions whether it is complete for that particular location of transducer, the fluid focus lens can be adjusted to a shallower depth and therapy can be delivered in this new direction (step 214). The fluid focus lens can be adjusted as desired to steer the beam in elevation and in lateral dimensions. The extent of the steering is determined by the transducer aperture, chosen fluids, and the fluid focus lens height and design (i.e. a typical 6 mm diameter transducer with a 5 mm lens height may give about a +/−22 degree steering capability from the center axis, covering approximately 45 degrees in total). Once all the steering is completed at the initial transducer position, then the transducer can be rotated (step 216), and translated to a new position to continue the therapy, repeating the focusing and repositioning until all of the prostate has been treated, with appropriate modifications of the fluid focus lens as appropriate.

The use of the fluid focus lens technology allows for more controlled treatment by adjusting steering and focus along the beam direction and allows for broad and tight therapy beams. Additionally, the treatment time can be shortened compared to current transducer single element designs because the fluid focus steering ability enables more of the prostate to be covered before mechanically translating/rotating it to a new position.

The invention thus enables fine adjustment of an ultrasound therapy beam to deliver therapy for various prostate sizes and shapes while avoiding damage to critical structures such as the rectal wall and nerve bundles. The same element can be used to create both diverging beams for a slow and conservative treatment (e.g. towards posterior side) as well as converging beams for faster and/or deeper treatment (e.g. towards anterior side).

In further embodiments, multiple fluid focus lenses can be used on a single therapy element, as described with reference to FIGS. 5a and 5b, to enable aperture changes that vary the depth-of-field of the therapy beam and the resolution by changing the aperture size. The smaller aperture can deliver energy over a larger resolution cell than the larger aperture defined by the physical size of the therapy element.

A combination of single or few-element therapy transducers and ultrasound imaging transducers can be designed for prostate therapy, monitoring, and assessment with fluid focus lenses in the transurethral device. In such an embodiment, the therapy and imaging elements could be different or could be the same. Preferentially, the imaging would be performed before, after, or intermittently during the therapy.

Although described with reference to the prostate, other ultrasound therapy treatments are also contemplated such as head, neck, and gynecological.

The invention can be used for treating both prostate cancer and benign prostatic hyperplasia. The invention can be used along with other treatments, especially for patients where more invasive treatments such as radiation have failed or in combination with localized drug delivery, for example to use the ultrasound therapy energy to cavitate one or more therapeutic bubbles or nanoparticles at the localized area. Treatments can be repeatedly performed if so desired. The invention is also useful in other applications where anatomically narrow access areas only are available, and the invention is not intended to be limited to prostate treatment. For example, other scenarios where transurethral access is required, such as treatment of male and female bladder cancer, are suitable for treatment with the system and method described herein. Other scenarios where fine control of ultrasound delivery may be useful for efficacious treatment include intra-cervix ultrasound therapy, uterine embolization ablation, arterial neck access to certain areas of the head or neck, access into another organ via a blood vessel, or use in an invasive therapy such as into the liver where it is desired to make a small diameter incursion into an organ or other body tissue.

The invention, including the steps of the methodologies described above, can be realized in hardware, software, or a combination of hardware and software. The invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The invention, including the steps of the methodologies described above, can be embedded in a computer program product. The computer program product can comprise a computer-readable storage medium in which is embedded a computer program comprising computer-executable code for directing a computing device or computer-based system to perform the various procedures, processes and methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Therefore, it is intended that the disclosure not be limited to the particular embodiment(s) disclosed as the best mode contemplated for carrying out this invention, but that the invention will include all embodiments falling within the scope of the appended claims.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims.

What is claimed is:

1. A system for delivering ultrasound therapy to a tissue comprising:
    an ultrasonic applicator including a transducer element, wherein the transducer element is configured to operate in an imaging mode to intermittently image the tissue to acquire signals used for forming images of the tissue to be treated;
    three variable focus lenses attached to said transducer element, wherein focus of the three variable focus lenses is controlled by lens voltage signals;
    a motion controller configured to move the ultrasonic applicator in at least one of a rotational direction and an axial direction; and
    a treatment controller configured to control the voltage signals applied to the three variable focus lenses based on the images of the tissue to direct an ultrasonic treatment beam emitted by said transducer element for treating the tissue, and
    wherein the three variable focus lenses are placed side-by-side over the transducer element for forming a main beam on an optical axis of the three variable focus lenses, each of the three variable focus lenses being separately controllable by the treatment controller to change an aperture of the main beam on the optical axis and form divergent beams at sides of the main beam that diverge from the optical axis and have a lower energy than the main beam by changing meniscuses of the three variable focus lenses to result in adjacent end points of two adjacent lenses of the three variable focus lenses being at different locations along a boundary of the two adjacent lenses including the adjacent end points.

2. The system according to claim 1, wherein each of the three variable focus lenses includes a fluid focus lens attached to the transducer element.

3. The system according to claim 1, wherein a plurality of transducer elements are provided in the ultrasonic applicator.

4. The system according to claim 3, wherein the plurality of transducer elements are arranged axially along the ultrasonic applicator.

5. The system according to claim 1, further comprising an imager configured to provide at least one of pre-treatment planning images and feedback images during treatment.

6. The system according to claim 1, further comprising an imager which is selected from the group consisting of an endo-rectal or vaginal ultrasound imaging system, an ultrasound imaging system having an external transducer, a magnetic resonance imaging system with or without the capability to perform MRI thermometry, a PET imaging system, a CT imaging system, a contrast-enhanced imaging system, a thermal monitoring system, and a tissue elasticity monitoring system, and combinations thereof.

7. The system according to claim 1, wherein the treatment controller is further configured to control a driving signal to the transducer element at least partially determined by the images.

8. The system according to claim 1, wherein the treatment controller is further configured to control the motion controller to control movement of the applicator.

9. The system according to claim 1, further comprising a user interface enabling an operator to visualize the images and to modify actions of the treatment controller.

10. The system according to claim 1, wherein the ultrasonic applicator is configured for transurethral accessed treatment.

11. A method of changing an aperture of a main beam for treating a tissue of interest comprising the acts of:

placing an ultrasonic applicator with one or more ultrasound transducer elements near to the tissue of interest;

exciting at least one transducer element of the one or more ultrasound transducer elements with a driving signal;

monitoring effect of the exciting act through images of the tissue to be treated obtained from signals obtained by the at least one transducer element which is configured to operate in an imaging mode to intermittently image the tissue to acquire the signals for forming the images of the tissue to be treated;

controlling the aperture of the main beam emitted from a single ultrasound transducer element of the at least one transducer element by adjusting voltages applied to three variable focus lenses placed side-by-side over the single ultrasound transducer element based on information from the images;

moving or rotating the ultrasonic applicator to cover therapy at substantially different regions in the tissue for treating the substantially different regions of the tissue; and separately controlling each of the three variable focus lenses to change the aperture of the main beam on an optical axis and form divergent beams at sides of the main beam that diverge from the optical axis and have a lower energy than the main beam by changing meniscuses of the three variable focus lenses to result in adjacent end points of two adjacent lenses of the three variable focus lenses being at different locations along a boundary of the two adjacent lenses including the adjacent end points.

12. The method according to claim 11, wherein each of the three variable focus lenses includes a fluid focus lens.

13. The method according to claim 11, wherein the acts of controlling and moving or rotating are based upon information received from the images.

14. The method according to claim 11, further comprising the act of obtaining planning images of the tissue to be treated prior to treatment.

15. The method according to claim 11, further comprising providing further images of the tissue to be treated including contrast-enhanced ultrasound images, magnetic resonance images, magnetic resonance thermometry images, PET images, CT images, thermal monitoring images, and tissue elasticity monitoring images, and any combinations thereof.

16. The method according to claim 11, further comprising the act of controlling the driving signal to the at least one ultrasound transducer element at least partially based on information from the images.

17. The method according to claim 11, further comprising the act of providing a user interface to enable an operator to visualize the images and to modify actions of a treatment controller that controls the voltages applied to the three variable focus lenses.

18. The method according to claim 17, wherein the treatment controller further controls the driving signal to the at least one ultrasound transducer, which is modifiable by the operator.

* * * * *